United States Patent [19]

Scholz et al.

[11] 4,238,618
[45] Dec. 9, 1980

[54] PROCESS FOR THE PREPARATION OF DIACYLATED 4-IMIDAZOLIN-2-ONES

[75] Inventors: Karl-Heinz Scholz; Willy Hartmann; Hans-Georg Heine, all of Krefeld, Fed. Rep. of Germany

[73] Assignee: Bayer Aktiengesellschaft, Leverkusen, Fed. Rep. of Germany

[21] Appl. No.: 884,520

[22] Filed: Mar. 8, 1978

[30] Foreign Application Priority Data

Mar. 26, 1977 [DE] Fed. Rep. of Germany ....... 2713431

[51] Int. Cl.³ ............................................. C07D 233/70
[52] U.S. Cl. .................................... 548/320; 548/302; 548/317; 548/319
[58] Field of Search .......................................... 548/320

[56] References Cited

U.S. PATENT DOCUMENTS

| | | | |
|---|---|---|---|
| 2,441,935 | 5/1948 | Duschinski | 548/320 |
| 2,694,726 | 11/1954 | Anspon | 260/561 HL |

OTHER PUBLICATIONS

Roberts et al., Basic Principles of Organic Chemistry, pp. 91–92, 203, 308, 320–321, 935, Benjamin, N.Y. 1965.

*Primary Examiner*—Alan L. Rotman
*Assistant Examiner*—Natalia Harkaway
*Attorney, Agent, or Firm*—Sprung, Felfe, Horn, Lynch & Kramer

[57] ABSTRACT

A process for the preparation of a diacylated 4-imidazolin-2-one of the formula

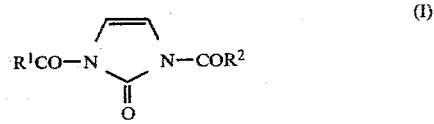

(I)

wherein
$R^1$ and $R^2$ independently represent hydrogen, optionally substituted alkyl, cycloalkyl, aryl and alkoxy, which comprises contacting a compound of the formula of II

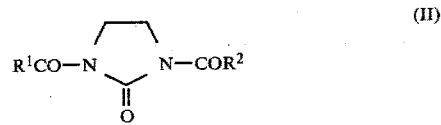

(II)

wherein
$R^1$ and $R^2$ of the previously assigned significance with a source of chlorine at a temperature from 20° to 150° C. in the presence of a radical forming agent or under ultra-violet light and thereafter dehydrohalogenating or dehalogenating the resultant chlorinated product the diacylated 4-imidazolin-2-ones prepared by the process are useful for photochemical cycloadditions and as intermediates for the preparation of compounds in the biotin series.

6 Claims, No Drawings

PROCESS FOR THE PREPARATION OF DIACYLATED 4-IMIDAZOLIN-2-ONES

BACKGROUND OF THE INVENTION

1. Field of the Invention

The invention relates to a process for the preparation of 1,3-diacyl-4-imidazolin-2-ones and to their use for cyclo-additions.

2. Discussion of the Prior Art

The preparation of 1,3-diacetyl-4-imidazolin-2-one is known from J. Chem. Soc. 95, 1329 (1909). Thus, the reaction of 4-imidazolin-2-one with acetic anhydride, on heating, gives 1,3-diacetyl-4-imidazolin-2-one. However, 4-imidazolin-2-one required as the starting compound for this reaction is difficult to obtain and in larger amounts, in particular, is hardly accessible. Thus, for example, the reaction of α-aminoacetaldehyde diethylacetal with cyanic acid, followed by cyclisation, gives 4-imidazolin-2-one, but this reaction sequence is greatly dependent on the reaction parameters (concentration, temperature and the like) (J. Amer. Chem. Soc. 68, 2351 (1946) and can only be carried out on a sizeable scale with substantial losses in yield.

The reaction of tartaric acid or dihydroxymaleic acid with urea in concentrated sulphuric acid or oleum to give 4-imidazolin-2-one-4-carboxylic acid, followed by decarboxylation (J. Amer. Chem. Soc. 54, 3413 (1932), C.A. 78, 58. 318 m (1973)) is also technically rather unsuitable for the preparation of sizeable amounts of 4-imidazolin-2-one (large volumes of reaction solution, and elimination of $CO_2$). Since furthermore, during the subsequent esterification, unconverted 4-imidazolin-2-one or only partially esterified 4-imidazolin-2-one, such as, for example, 1-acetyl-4-imidazolin-2-one, specifically greatly retards or even inhibits photochemical cycloadditions with the 1,3-diacyl-4-imidazolin-2-ones (Chem. Ber. 100, 3961 (1967); 101, 3688 (1968)) it was desirable to provide a process for the synthesis of 1,3-diacyl-4-imidazolin-2-ones, especially of 1,3-diacetyl-4-imidazolin-2-one, in which the two acyl radicals are already present in the starting compound and do not undergo any change during the reaction to give the 1,3-diacyl-4-imidazolin-2-one.

SUMMARY OF THE INVENTION

A process for the preparation of diacylated 4-imidazolin-2-ones of the general formula

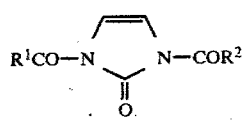

in which $R^1$ and $R^2$ may be identical or different and represent hydrogen, optionally substituted alkyl, cycloalkyl, aryl or alkoxy has been found, which is characterised in that a compound of the general formula $$R^1CO-N \overset{\diagup\!\!\!=\!\!\!\diagdown}{\underset{\underset{O}{\|}}{\phantom{X}}} N-COR^2 \quad (II)$$

in which $R^1$ and $R^2$ have the abovementioned meaning is chlorinated at temperatures from 20° to 150° C. in the presence of a radical-forming agent or of UV light and the chlorination product is subsequently dehydrohalogenated or dehalogenated.

The process according to the invention can be illustrated by the following reaction scheme:

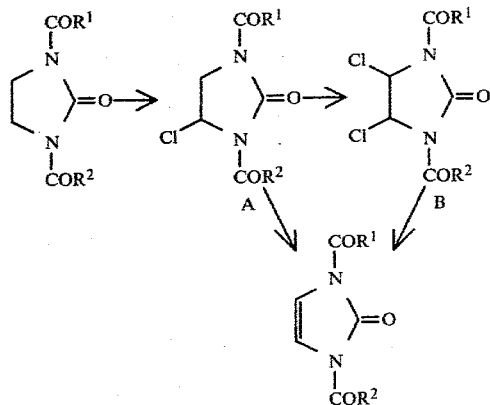

Route A comprises a dehydrohalogenation and route B a dehalogenation, for example by means of metals.

Suitable radicals $R^1$ and $R^2$ in the above formulae are hydrocarbon radicals with up to 10 C atoms, for example alkyl radicals, such as methyl, ethyl, n-propyl, iso-propyl, n-butyl, iso-butyl, tert.-butyl, n-pentyl, iso-pentyl, 2-methylpentyl, 3-methylpentyl, n-hexyl, iso-hexyl, n-octyl and iso-octyl, as well as alkyl radicals substituted by $C_1$—$C_2$ alkoxy, such as β-ethoxyethyl, or alkyl radicals substituted by halogen, such as fluorine, chlorine or bromine, for example β-chloroethyl, trifluoromethyl and chloromethyl; cycloalkyl radicals, such as cyclopentyl and cyclohexyl or cyclohexyl radicals substituted by $C_1$-$C_4$-alkyl groups, such as 4-methylcyclohexyl and 4-tert.-butyl-cyclohexyl; aryl radicals, such as phenyl, or phenyl substituted by $C_1$-$C_4$-alkyl, $C_1$-$C_2$-alkoxy or halogen, especially chlorine, such as 4-chlorophenyl, 4-tert.-butyl-phenyl and 1- and 2-naphthyl; and alkoxy radicals, such as methoxy, ethoxy, propoxy and butoxy.

The 1,3-diacyl-imidazolidin-2-ones required as starting compounds for the process according to the invention, and especially 1,3-diacetyl-imidazolidin-2-one, are in themselves known (J. Chem. Soc. 1964, 176) or can be prepared in accordance with known processes.

These 1,3-diacyl-imidazolidin-2-ones can be chlorinated in the presence of a radical-forming agent or of UV light and optionally in the presence of a solvent which is inert under the reaction conditions, at temperatures from about 20° to 150° C., preferably 50° to 100° C., and the chlorination product can subsequently be dehydrohalogenated or dehalogenated. The dehydrohalogenation can be effected by heating in vacuo to temperatures from about 100° to 250° C., preferably 130° to 170° C., or by reaction with a tertiary amine in an aprotic organic solvent at temperatures in the range from 20° to 120° C., preferably at 30° to 100° C. The dehalogenation can be effected by heating with metals, for example zinc or iron and/or with metal carbonyls, such as nickel tetracarbonyl, molybdenum hexacarbonyl or iron pentacarbonyl, in a suitable solvent in the presence of a catalyst at temperatures from about 20° to 120° C., preferably at 30° to 100° C.

As radical forming agents for the process according to the invention one can employ, for example, peroxides, peracid esters or azoalkanes. As examples there may be mentioned: benzoylperoxide, perbenzoic acid-tert.-butylester and azodi-isobutyronitrile.

As starting compounds for the process according to the invention one can employ those 1,3-diacylated imidazolidin-2-ones of which the acyl radicals $R^1$ and $R^2$ are substantially stable (inert) under the chlorination conditions used. As examples there may be mentioned: 1,3-diacetyl-, 1,3-di-n-propionyl-, 1,3-di-n-butyryl- and 1,3-dimethoxy-carbonyl-imidazolidin-2-one, 1,3-diacetyl-imidazolidin-2-one being preferred.

Chlorine or sulphuryl chloride, as well as mixtures of chlorine and sulphuryl chloride, can be used for the chlorination. As is usual for the monochlorination, the chlorination agent is employed in about equimolar amounts. For the dichlorination, about two mol equivalents of chlorine are used. If the chlorine is carried out with sulphuryl chloride, the latter can be employed in excess (about 2 to 10 mol equivalents, preferably 3 to 6 mol equivalents).

All organic solvents which are inert under the reaction conditions can be used as solvents to be employed for the chlorination. Aprotic organic solvents, such as halogenated hydrocarbons with up to 8 C atoms, for example chloroform, methylene chloride, carbon tetrachloride, hexachlorobutadiene and chlorobenzene, should be mentioned preferentially. A further possible solvent is carbon disulphide. Carbon tetrachloride has proved a particularly suitable solvent.

Dehydrohalogenation (Route A)

Organic solvents which are inert under the reaction conditions, especially aprotic organic solvents, such as ethers, for example diethyl ether, dibutyl ether, tetrahydrofurane, dioxane and 1,2-dimethoxyethane, esters of aliphatic or aromatic carboxylic acids with up to 10 C atoms, for example acetic acid esters of lower alcohols, such as ethyl acetate and butyl acetate, and optionally substituted aromatic hydrocarbons with up to 10 C atoms, such as benzene, toluene, chlorobenzene and fluorobenzene, may be used for the dehydrohalogenation. Preferably, diethyl ether, dibutyl ether, tetrahydrofurane or dioxane is used as the solvent.

Trialkylamines, such as triethylamine, N,N-dimethylcyclohexylamine and N,N-dimethylbenzylamine, N,N-dialkylamines, such as N,N-dimethylaniline, heterocyclic bases such as pyridine and picolines, and diazabicycloalkenes, for example 1,5-diazabicyclo[4,3,0]-non-5-ene, have in particular proved suitable tertiary amines for the dehydrohalogenation. Preferably, triethylamine is used.

The process according to the invention is generally carried out as follows: the 1,3-diacylated imidazolidin-2-ones of the formula (II), or their solutions in an aprotic organic solvent, preferably carbon tetrachloride, are heated to the required reaction temperature and are kept at this temperature during the subsequent addition of chlorine or sulphuryl chloride. The radical chlorination is started by adding a radical-forming agent, for example azodiisobutyronitrile, or by UV light. Chlorine or sulphuryl chloride are metered in at the rate at which they are consumed, and the rate of addition can be easily and simply regulated, in accordance with the evolution of gas during the reaction, with the aid of known methods of measurement. In general, the reaction mixture has to be warmed in order to maintain the reaction temperature.

The working up of the reaction mixture which in addition to the reaction product may also contain residual starting compound, hydrogen chloride and possibly sulphur dioxide, in solution, is carried out in a manner which is in itself known. For example, the products which are lower-boiling than the 1,3-diacyl-4-chloro-imidazolidin-2-one can be distilled off, if appropriate under reduced pressure. However, it is also possible to elute a large proportion of these products with water; in that case, the reaction product remains in the organic phase.

The crude reaction product obtained can optionally be purified by crystallisation; however, it is normally employed directly for the dehydrohalogenation. The thermal dehydrohalogenation is carried out, for example, by introducing the crude 1,3-diacyl-4-imidazolidin-2-one dropwise into a flask warmed to about 100°-250° C. and distilling off the resulting reaction product under reduced pressure. The product can subsequently be purified in the usual manner, for example by distillation, if appropriate under reduced pressure, or by recrystallisation.

The base-catalysed dehydrohalogenation can be carried out, for example, by dissolving the crude 1,3-diacyl-4-chloro-imidazolidin-2-one in an aprotic organic solvent, for example diethyl ether, dibutyl ether of dioxane, and adding about 1 to 5 mols of the tertiary amine, preferably 1.5 to 3 mols, per mol of chlorine compound, in portions to the solution whilst stirring, at the boiling point of the solvent. In general, the elimination of the hydrogen chloride has ended after 20 to 30 hours. After separating off the hydrochloride, 1,3-diacyl-4-imidazolin-2-one is isolated from the solution. The isolation and purification can be carried out as described above, by distillation and/or recrystallisation.

Mixtures of ethers, such as diethyl ether or dibutyl ether, and alkanes, for example n-hexane and/or petroleum ether, have proved particularly suitable for the recrystallisation of the 1,3-diacyl-4-imidazolin-2-ones. If appropriate, the solution of the reaction product can be purified, before crystallisation, with the aid of customary clarifying agents of absorbents, such as charcoal or kieselguhr.

Dehalogenation (Route B)

The dehalogenation can be carried out in the presence of inert solvents or diluents or mixtures of solvents or diluents.

Inert organic solvents or diluents which may be mentioned are aliphatic and cycloaliphatic hydrocarbons with up to 10 carbon atoms, preferably with up to 8 carbon atoms, such as n-hexane, iso-octane, decalin, cyclohexane and methyl-cyclohexane, as well as aromatic hydrocarbons with up to 8 carbon atoms, such as benzene, toluene and xylene, aliphatic and cycloaliphatic ethers with up to 8 carbon atoms, such as diethyl ehter, dibutyl ether, tetrahydrofurane, dioxane and 1,2-dimethoxyethane, and esters of aliphatic and aromatic carboxylic acids with up to 10 carbon atoms, preferably with up to 7 carbon atoms, such as ethyl acetate, butyl acetate and ethyl benzoate.

Further solvents or diluents which can also be used are protic solvents or diluents, such as acetic acid, methanol and ethanol. These may be used by themselves or as a mixture with the previously mentioned aprotic solvents or diluents.

Diethyl ether and/or dibutyl ether are particularly preferred as the solvent or diluent.

Suitable catalysts for the dehalogenation with metals or metal carbonyls are, in particular, dipolar aprotic compounds, such as, for example, dimethylformamide, dimethylacetamide and hexamethylphosphoric acid triamide.

To prepare the 1,3-diacyl-4,5-dichloro-imidazolidin-2-ones, the procedure followed is in principle as described for the monochlorination to give the 4-chloro-1,3-diacyl-imidazolidin-2-one. Advantageously, about two mol equivalents of chlorine are used in the photochlorination, to avoid chlorinating the acyl group. When carrying out the chlorination with sulphuryl chloride, the observation of this reaction parameter is not so essential. Rather, even with a large excess of sulphuryl chloride, the reaction in the presence of a radical starter gives virtually only the desired 1,3-diacyl-4,5-dichloro-imidazolidin-2-one.

These chlorination products can also optionally be purified by distillation or crystallisation. In many cases, the crude chlorination products can be used for the further reaction to give the 1,3-diacyl-4-imidazolin-2-ones.

The 1,3-diacyl-4,5-dichloroimidazolidin-2-ones obtainable by chlorination can be dehalogenated by, for example, dissolving them in a suitable solvent and adding about 1 to 3 mol equivalents of the dehalogenating agent in portions to the solution at a slightly elevated temperature. Preferably, zinc which has been activated in accordance with J. Org. Chem. 29, 2049 (1964) is used. The dehalogenation can be accelerated by adding from about 1 to 5% by weight of dimethylformamide, relative to the amount of the dichloro-compound employed. Preferably, the catalyst is introduced into the reaction solution before adding the dehalogenating agent. The progress of the reaction can be followed in various ways, for example by analysing the content of starting material and end product by gas chromatography. In general, the elimination of the halogen has ended after 6 to 10 hours. If diethyl ether is used as the solvent, the 1,3-diacyl-4-imidazolin-2-one formed often crystallises out merely on cooling the solution. Advantageously, a small amount of a solubilising agent, such as, for example, the aromatic hydrocarbons, such as benzene and/or toluene, is therefore added to the reaction solution before working up, so that the 1,3-diacyl-4-imidazolin-2-one formed remains in solution.

The amount of the solubilising agent can be easily determined by preliminary experiments.

Unconverted metal or metal chloride can be separated off by filtration. However, it is advantageous to add water to the reaction solution before filtration in order to dissolve the metal salts formed and to deactivate unconverted metal. By doing this, the metal is often obtained in a form which can be separated off more easily. The further working up can be effected by washing the filtered solution with water and dilute sodium bicarbonate solution, drying and evaporation. By doing so, the 1,3-diacyl-4-imdazolin-2-one is often obtained in a purity which is such that in general further purification by crystallisation or distillation is superfluous.

The 1,3-diacyl-4-imidazolin-2-ones which are easily obtainable by the process according to the invention are valuable starting compounds for numerous further reactions. Thus, the base-catalysed solvolysis of 1,3-diacetyl-4-imidazolin-2-one in methanol quantitatively gives 4-imidazolin-2-one which is readily soluble in water and which, after distilling off the solvent and the methyl acetate formed, remains solvent-free. In turn, 4-imidazolin-2-one is known to be a valuable intermediate product for numerous synthesis in the biotin series (J. Amer. Chem. Soc. 68, 2350 (1946)).

As mentioned, 1,3diacyl-4-imidazolin-2-ones are obtained in accordance with the process according to the invention in a high purity, which is of great importance especially for photochemical cycloadditions with this class of compound (Chem. Ber. 100, 3961 (1967)). Thus, for example, exposure to light of 1,3-diacetyl-4-imidazolin-2-one together with olefins, such as, for example, ethylene, propylene, isobutylene, neohexene, cyclopentene, allene, cyclohexene, vinyl acetate, methyl vinyl ether, acetylene and 1,2-bis-(trimethylsiloxy)-ethylene, in the presence of a sensitiser, such as, for example, acetone or dicyclopropyl ketone, smoothly gives the corresponding [2+2]-cycloadducts of the general formula (III) in accordance with the following equation:

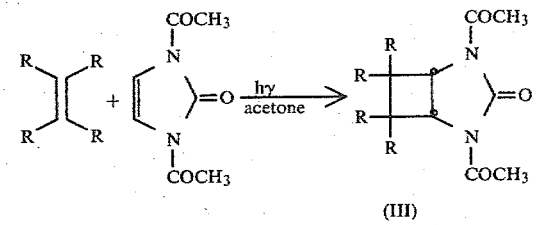

The cycloadducts of the general formula (III) can be converted with potassium carbonate/water or with sodium methylate/methanol into the cyclic ureas of the general formula (IV).

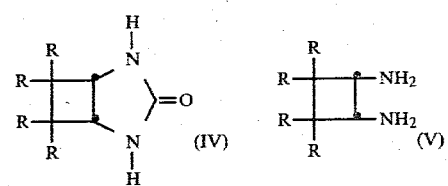

More vigorous saponification (for example potassium hydroxide/methanol) smoothly gives the 1,2-diamines of the four-membered ring series [general formula (V)], of which hitherto only the parent compound, 1,2-diaminocyclobutane, has been known (J.Amer.Chem.-Soc. 64, 2696 (1942)).

It follows from the course of the reaction that the 1,2-diamines are obtained as cis-isomers.

The photochemical reaction described is not restricted to 1,3-diacetyl-4-imidazolin-2-one but also succeeds with other 1,3-diacyl-4-imidazolin-2-ones. The 1,3-diacyl-4-imibazolin-2-ones which are smoothly and readily obtainable by the process according to the invention, even in substantial amounts, can accordingly be used as starting compounds for syntheses of 1,2-diaminocyclobutanes which are virtually unknown in the literature.

1,3-Diacyl-4-imidazolin-2-ones can also be employed for other cycloadditions. Thus 1,3-diacetyl-4-imidazolin-2-one reacts smoothly with 1,3-dienes, such as, for example, 1,3-cyclohexadiene, cyclopentadiene or anthracene, to give the corresponding Diels-Alder adducts ([2+4]-cycloaddition) which by selective hydrolysis give the corresponding imidazolidin-2-ones and, finally, the corresponding cis-1,2-diamines. Numerous compounds of the general formulae (VI-VIII) which otherwise can only be prepared by an expensive method, are accessible in this way.

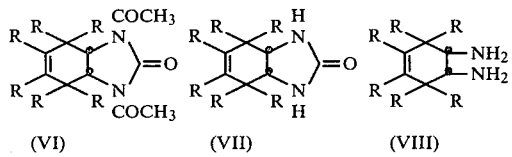

(VI)          (VII)         (VIII)

The 1,3-diacyl-4-imidazolin-2-ones obtainable in accordance with the process of the invention can be reacted with suitable partners to give [2+1]-cycloadducts (carbene reaction) and to give [3+2]-cycloadducts (1,3-dipolar addition). They are therefore, in general terms, very valuable intermediate products for the preparation of a plurality of new compounds which are characterized in that they contain a 1,2-diamino grouping.

The process according to the invention will be presented with the aid of the examples which follow, without however restricting it thereto.

EXAMPLE 1

A total of 2.0 g of azodiisobutyronitrile and 2,850 g (21 mols) of sulphuryl chloride is introduced into a solution of 850 g (5.0 mols) of 1,3-diacetyl-imidazolidin-2-one in 200 ml of chloroform at the boil in the course of 4 to 6 hours, whilst stirring, in such a way that a brisk evolution of gas occurs. After stirring for 3 hours under reflux, the solvent and excess sulphuryl chloride are distilled off under reduced pressure. The residue which remains is 1,160 g of 1,3-diacetyl-4,5-dichloro-imidazolidin-2-one which crystallises and which is reacted further, as the crude product. Melting point 79°–81° (from ether).

$C_7H_8Cl_2N_2O_3$ Calculated: C 35.16; H 3.37; N 11.72; Cl 29.66; (239.1) Found: 35.2; 3.36; 11.7; 29.9; IR (KBr): 1,730 and 1,770 cm$^{-1}$ (CO)

NMR (CDCl$_3$): $\tau$=3.77 s (2H) and 7.40 ppm s (6H).

EXAMPLE 2

A solution of 170.5 g (1.0 mol) of 1,3-diacetylimidazolidin-2-one in 1,500 ml of carbon tetrachloride is heated to 80° C. in a four-necked flask equipped with a reflux condenser, internal thermometer, stirrer, gas inlet tube and immersed sleeve. Dry chlorine gas is passed into this solution whilst subjecting it to internal UV irradiation. (Philips HPK 125 W mercury high pressure lamp). After 2.1 mols of chlorine have been taken up, the chlorination is discontinued. The solvent is distilled off under reduced pressure and 247 g of a light yellow oil are obtained; on addition of diethyl ether, this oil gives 132 g of colourless crystals of melting point 80°–81° C.

EXAMPLE 3

1.2 g of azodiisobutyronitrile and 74.5 g (0.5 mol) of sulphuryl chloride are introduced into a solution of 85.3 g (0.5 mol) of 1,3-diacetyl-imidazolidin-2-one in 250 ml of chloroform at the boil, in the course of 2 hours, whilst stirring. After stirring for 3 hours under reflux, the solvent and unconverted sulphuryl chloride are distilled off under reduced pressure. 101 g of crude 1,3-diacetyl-4-chloro-imidazolidin-2-one remain as the residue, in the form of a light brown clear oil containing 16.4% of chlorine (calculated: 17.3% of Cl).

EXAMPLE 4

170.5 g (1.0 mol) of 1,3-diacetyl-imidazolidin-2-one in 1,500 ml of carbon tetrachloride are photochlorinated with 1.1 mols of chlorine in accordance with Example 2. Evaporating the solution under reduced pressure gives 218 g of a light yellow oil which on the evidence of the NMR spectrum contains more than 85% of 1,3-diacetyl-4-chloro-imidazolidin-2-one.

109 g of the crude product are heated under reflux for 3 hours under reduced pressure (12 mm Hg) and are worked up after complete conversion. For this purpose, the contents of the flask are dissolved in benzene and the solution is washed successively with water, with dilute sodium bicarbonate solution and again with water. Drying the solution over sodium sulphate and evaporating it in vacuo gives 69 g of colourless crystals which when recrystallized from ether give 48 g of 1,3-diacetyl-4-imidazolin-2-one.

75 g (0.75 mol) of triethylamine are added dropwise, whilst stirring, to 108 g of the crude chlorination product in 200 ml of dry ether, at the boil. After stirring for 48 hours under reflux, the reaction mixture is filtered, the residue is thoroughly eluted with ether and the combined filtrates are evaporated. 73 g of a crystalline crude product are obtained and are dissolved in benzene and filtered over silica gel. Concentration of the eluate in vacuo, and fractional crystallisation, gives 51 g of 1,3-diacetyl-4-imidazolin-2-one.

EXAMPLE 5

Activated zinc (from 63.5 g (1.0 mol) of zinc), prepared in accordance with J.Org.Chem. 29, 2049 (1964), are added in portions to a boiling solution of 119.5 g (0.5 mol) of recrystallised 1,3-diacetyl-4,5-dichloro-imidazolidin-2-one and 8 ml of dimethylformamide in 400 ml of dry diethyl ether and the mixture is heated under reflux until conversion is complete (16 hours). After the reaction solution has cooled, 200 ml of water are added to it, and the mixture is filtered. The filter cake is washed with 3×100 ml of benzene and the organic phases are combined and washed until they give a neutral reaction. Drying over sodium sulphate and evaporation gives 80.0 g (about 95%) of 1,3-diacetyl-4-imidazolin-2-one of melting point 106° C., identical with a sample prepared independently in accordance with J.Amer.Chem. Soc. 54, 3413 (1932).

If instead of the recrystallised 1,3-diacetyl-4,5-dichloro-imidazolidin-2-one the crude product from the photochlorination, obtained in accordance with Example 1, is employed, a batch of equal size gives 84% (relative to 1,3-diacetyl-imidazolidin-2-one) of 1,3-diacetyl-4-imidazolin-2-one.

EXAMPLE 6

A total of 65.3 g of zinc powder is added in portions over the course of 4 hours to a solution of 65.0 g (0.27 mol) of 1,3-diacetyl-4,5-dichloro-imidazolidin-2-one in 275 ml of glacial acetic acid at 20° to 30° C., whilst stirring. The mixture is stirred for a further 12 hours at 20° C. and is filtered, and the filtrate is diluted with 1,000 ml of water and extracted with benzene. Washing the benzene extract with water and dilute sodium bicarbonate solution and drying over magnesium sulphate gives, on evaporation, 33.4 g of a crystalline residue. Sublimation at 100° C./12 mm Hg gives 22.1 g (49%) of 1,3-diacetyl-4-imidazolin-2-one of melting point 103°–106° C. The residue from the sublimation is dissolved in hot benzene and on cooling the solution to 20° C. 7.7 g of colourless crystals of melting point 215° C. (sublimation from 205° C. onwards) are isolated. 4,5-Diacetoxy-1,3-diacetyl-imidazolidin-2-one.

$C_{11}H_{14}N_2O_7$ Calculated: C 46.15; H 4.93; N 9.79; (286.2) Found: 46.1; 4.88; 10.2.

EXAMPLE 7

0.3 g of sodium methylate is added to a solution of 8.4 g (0.05 mol) of 1,3-diacetyl-4-imidazolin-2-one in 60 ml of methanol and the mixture is heated under reflux for 4 hours. On cooling, 3.0 g of 4-imidazolin-2-one of melting point 261°–262° C. crystallise out.

Evaporation of the filtrate to one-third of its volume, and cooling the solution, gives a further 1.15 g of 4-imidazolin-2-one.

EXAMPLE 8

A solution of 5.75 g (0.034 mol) of 1,3-diacetyl-4-imidazolin-2-one and 5.0 mol of 1,3-cyclohexadiene in 5 ml of benzene and 15 ml of dioxane is heated for 20 hours to 170°–180° C. in a bomb tube. Evaporating the solution and chromatographing the residue on silica gel successively gives 1.0 g of dimer of 1,3-cyclohexadiene, 1.0 g of 1,3-diacetyl-4-imidazolin-2-one and 4.3 g of Diels-Alder adduct. Melting point 185°–186° (from ethanol).

$C_{13}H_{16}N_2O_3$ Calculated: C 62.89; H 6.50; N 11.23; (248.2) Found: 63.2; 6.28; 11.4.

EXAMPLE 9

A solution of 58.8 g (0.35 mol) of 1,3-diacetyl-4-imidazolin-2-one and 58 ml of dicyclopentadiene in 58 ml of dioxane is heated for 20 hours to 170°–180° C. in an autoclave. After evaporating the solution and distilling off unconverted starting compounds, a crystalline residue (70.2 g) is obtained, which according to NMR (CDCl$_3$) consists of the 2:1 adduct of cyclopentadiene and 1,3-diacetyl-4-imidazolin-2-one. Crystallisation from ethanol gives a total of 44.1 g of colourless crystals of melting point 177°–179°. A further 12.2 g of cycloadduct of melting point 163°–170° are isolated from the mother liquor.

$C_{17}H_{20}N_2O_3$ Calculated: C 67.98; H 6.71; N 9.33; (300.4) Found: 67.95; 6.78; 9.76.

Hydrolysis in aqueous-alcoholic sodium hydroxide solution quantitatively gives the corresponding cyclic urea. Melting point 308°–311° (sealed capillary).

$C_{13}N_{16}N_2O$ Calculated: C 72.19; H 7.46; N 12.95; (216.3) Found: 72.1; 7.70; 12.65.

EXAMPLE 10

A solution of 16.8 g (0.1 mol) of 1,3-diacetyl-4-imidazolin-2-one and 27.3 g (0.1 mol) of hexachlorocyclopentadiene in 100 ml of xylene is heated for 24 hours under reflux. Unconverted starting compounds are distilled off under reduced pressure and the solid residue (33.2 g, ~68%) is recrystallised from cyclohexane. Yield: 30.1 g of colourless crystals. Melting point 173°–175°.

$C_{12}H_8Cl_6N_2O_3$ Calculated: C 32.65; H 1.81; Cl 48.3; N 6.35; (441) Found: 32.9; 2.01; 47.9; 6.46; NMR (CDCl$_3$): $\tau = 4.63$ s (2H) and 7.52 ppm s (6H).

EXAMPLE 11

A solution of 3.36 g (0.02 mol) of 1,3-diacetyl-4-imidazolin-2-one in 160 ml of acetone is saturated with ethylene at $-70°$ C. and is then illuminated for 40 hours in an immersed lamp apparatus, with the lamp sleeve made of Pyrex (Philips HPK 125 W mercury high pressure lamp). On evaporating the solution in vacuo and crystallising the residue from ether, 3.0 g (77%) of 2,4-diacetyl-2,4-diaza-bicyclo [3,2,0]heptan-3-one are obtained as colourless crystals of melting point 74°–76°.

$C_9H_{12}N_2O_3$ Calculated: C 55.09; H 6.77; N 14.28; (196.2) Found: 55.1; 6.53; 14.2; IR(KBr): 1,705 and 17.55 cm$^{-1}$.

If an identical batch is illuminated in an immersed lamp apparatus with a quartz lamp sleeve, 87% of the cycloadduct are obtained after 10 hours' illumination.

The following cycloadducts are accessible analogously: 6-methyl-2,4-diacetyl-2,4-diaza-bicyclo[3,2,0-]heptan-3-one, boiling point$_{0.25}$111°–115° (77%); 6,6-dimethyl-2,4-diacetyl-2,4-diaza-bicyclo[3,2,0]heptan-3-one, boiling point$_{0.4}$103°–104° (67%); 6-tert.-butyl-2,4-diacetyl-2,4-diaza-bicyclo[3,2,0]heptan-3-one, melting point 85°–86° (54%); 6,6,7,7-tetramethyl-2,4-diacetyl-2,4-diaza-bicyclo[3,2,0]heptan-3-one, melting point 79°–81° (78%); 6-methylene-2,4-diacetyl-2,4-diaza-bicyclo[3,2,0]heptan-3-one, melting point 109°–111° (71%); 6-methoxy-2,4-diacetyl-2,4-diaza-bicyclo[3,2,0]heptan-3-one, boiling point$_1$120–124 (68%), stereoisomers; 6-acetoxy-2,4-diacetyl-2,4-diaza-bicyclo[3,2,0]heptan-3-one, melting point 151°–153° (single stereoisomer) (82% total yield); 8,10-diacetyl-8,10-diaza-tricyclo[5,3,0,0$^{2,6}$]decan-9-one, melting point 148°–150° (single stereoisomer, yield: 40%); and 2',4'-diacetyl-spiro[-cyclopropane-1,6'-diaza-(2',4')-bicyclo[3,2,0]heptan-3'-one], melting point 63° (74%).

EXAMPLE 12

A solution of 100.0 g (0.51 mol) of 2,4-diacetyl-2,4-diaza-bicyclo[3,2,0]heptan-3-one, 750 ml of methanol and 1.0 g of sodium methylate is heated under reflux. After complete conversion (5 hours), the solution is concentrated in vacuo and the residue, in solution in chloroform, is filtered over silica gel. 56.0 g (98%) of 2,4-diazabicyclo[3,2,0]heptan-3-one are obtained as colourless crystals of melting point 146°–148° (from chloroform).

The following ureas are accessible analogously: 6-methyl-2,4-diaza-bicyclo[3,2,0]heptan-3-one, melting point 120°–124° (88%); 6,6-dimethyl-2,4-diaza-bicyclo[3,2,0]heptan-3-one, melting point 190°–191° (79%); 6-tert.-butyl-2,4-diaza-bicyclo[3,2,0]heptan-3-one, melting point 227°–229° (100%); 6,6,7,7-tetramethyl-2,4-diaza-bicyclo[3,2,0]heptan-3-one melting point 254° (sublimation) (78%); 6-methylene-2,4-diaza-bicyclo[3,2,0]heptan-3-one, melting point 100°–102° (100%); 8,10-diaza-tricyclo[5,3,0,0$^{2,6}$]decan-9-one, melting point 264°–268° (57%); 6-methoxy-2,4-diaza-bicyclo[3,2,0-]heptan-3-one, melting point 140° (60%); 6-hydroxy-2,4-diaza-bicyclo[3,2,0]heptan-3-one, melting point 128°–152° (stereoisomers) (81%); and spiro[cyclopropane-1,6'-diaza-(2',4')-bicyclo[3,2,0]heptan-3'-one, melting point 139°–140° (68%).

EXAMPLE 13

A solution of 21.3 g (0.11 mol) of 2,4-diaza-bicyclo [3,2,0]heptan-3-one and 122.0 g (2.18 mols) of potassium hydroxide in 300 ml of aqueous methanol (50% strength) is heated for 24 hours to 150° C. in a nickel autoclave. The mixture is then exhaustively extracted with ether in a Kutscher-Steudel apparatus. After acidifying the ether extract with concentrated hydrochloric acid, the solvent is stripped off in vacuo and cis-1,2-diamino-cyclobutane is liberated from the hydrochloride left, by adding potassium hydroxide and ether. Yield: 6.0 g (64%), colourless liquid, boiling point 142°–146°, $n_D^{20}$ 1.4820.

The following diamines are accessible analogously: 3-methyl-cis-1,2-diamino-cyclobutane, boiling point 152° (62%) (isomers); 3,3-dimethyl-cis-1,2-diamino-cyclobutane, boiling point 157° (50%); and 3,3,4,4-tetramethyl-cis-1,2-diamino-cyclobutane, boiling point 190° (68%).

EXAMPLE 14

A solution of diazomethane in ether (prepared from 200 g of N-nitrosomethylurea) is introduced in portions over the course of 3 days into a solution of 25.0 g (0.15 mol) of 1,3-diacetyl-4-imidazolin-2-one and 5.0 g of copper-I chloride in 250 ml of di-n-butyl ether at 80°–90°. The solution is then filtered, the residue is repeatedly eluted with benzene and the combined filtrates are concentrated in vacuo. Chromatography of the crude product on silica gel gives 10.3 g of unconverted 1,3-diacetyl-4-imidazolin-2-one and 3.6 g (about 20%) of 2,4-diacetyl-2,4-diaza-bicyclo[3,1,0]hexan-3-one as colourless crystals of melting point 134°–136° C. (from ether).

$C_8H_{10}N_2O_3$ Calculated: C 52.74; H 5.53; N 15.38; (182.2) Found: 52.7; 5.47; 15.4; (IR (KBr): 1,680, 1,695, 1,735 and 1,760 $cm^{-1}$.

EXAMPLE 15

A solution of 16.8 g (0.1 mol) of 1,3-diacetyl-4-imidazolin-2-one and 10.0 g (0.05 mol) of N,α-diphenyl-nitrone in 50 ml of benzene is heated for 40 hours under reflux. Evaporation in vacuo, and chromatography of the resulting residue (15.2 g) over silica gel with benzene gives 8.4 g (23%) of cycloadduct as colourless crystals of melting point 165°–166° C. (from chloroform).

$C_{20}H_{19}N_3O_4$ Calculated: C 65.74; H 5.24; N 11.50; (365.4) Found: 65.3; 5.10; 11.4; IR(KBr): 1,690, 1,710 and 1,770 $cm^{-1}$; NMR(CDCl$_3$): 2.80 m (10H), 3.80 d (1H), 4.55 s (1H), 5.10 d (1H), 5.55 s (3H) and 5.60 ppm s (3H).

Elution with methylene chloride/acetone (9:1) gives the isomeric cycloadduct (3.2 g (9%)) as colourless crystals of melting point 136°–138° (from ether).

Found: C 65.6; H 5.02; N 11.4; IR(KBr): 1,710 and 1,775 $cm^{-1}$; NMR (CDCl$_3$): 2.80 m (10H), 3.65 d (1H), 4.60 t (1H), 5.45 d (1H), 7.35 s (3H) and 7.85 ppm s (3H).

What is claimed is:

1. A process for the preparation of a diacylated 4-imidazolin-2-one of the formula

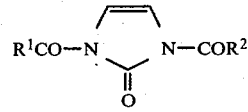

wherein
$R^1$ and $R^2$ independently represent hydrogen, alkyl which can be substituted by a $C_{1-2}$ alkoxy radical or a halogen, cycloalkyl which can be $C_{1-4}$ alkyl substituted, aryl which which can be $C_1$-$C_4$ alkyl or $C_1$-$C_2$ alkoxy or halogen substituted or alkoxy, the alkyl, cycloalkyl, aryl or alkoxy groups representing $R^1$ or $R^2$ having up to ten carbon atoms, which comprises contacting a compound of the formula

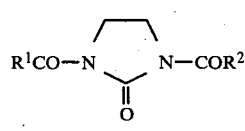

where
$R^1$ and $R^2$ have the previously assigned significance with about 2 mol equivalents of chlorine or 2 to 10 mol equivalents or sulphuryl chloride at a temperature from 20° to 150° C. in the presence of a peroxide, peracid ester or azoalkane radical forming agent or under ultra-violet light to dihalogenate the same and thereafter dehalogenating the resultant dihalogenated product in the presence of a metal or metal carbonyl compound selected from the group consisting of zinc, iron, nickel tetracarbonyl, molybdenum hexacarbonyl and iron pentacarbonyl.

2. A process according to claim 1 wherein said 1,3-diacyl-4-imidazolidin-2-one is 1,3-diacetyl-imidazolidin-2-one.

3. A process according to claim 1 wherein the reaction is carried out in the presence of ultra-violet light employing about 2 molar equivalents of chlorine whereby there is obtained a dihalogenated product and the resultant dihalogenated product is dehalogenated.

4. A process according to claim 1 wherein the compound of the formula II

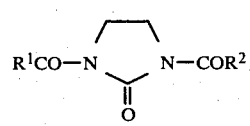

is reacted with 2 to 10 molar equivalents of sulphuryl chloride in the presence of a radical forming agent and the resultant chlorinated product is thereafter dehalogenated.

5. A process according to claim 3 wherein the dehalogenation is effected in the presence of activated zinc and dimethyl formamide as catalyst.

6. A process according to claim 4 wherein the dehalogenation is carried out in the presence of activated zinc and dimethyl formamide.

* * * * *

UNITED STATES PATENT AND TRADEMARK OFFICE
CERTIFICATE OF CORRECTION

PATENT NO. : 4,238,618
DATED : December 9, 1980.
INVENTOR(S) : Karl-Heinz Scholz; Willy Hartmann; Hans-Georg Heine It is certified that error appears in the above-identified patent and that said Letters Patent are hereby corrected as shown below:

Column    Line 9    36    "248.2" should be "248.3"

Signed and Sealed this

Seventh Day of April 1981

[SEAL]

Attest:

RENE D. TEGTMEYER

Attesting Officer    Acting Commissioner of Patents and Trademarks